United States Patent [19]
Labrie et al.

[11] Patent Number: 5,712,251
[45] Date of Patent: Jan. 27, 1998

[54] TREATMENT METHOD

[75] Inventors: Fernand Labrie, Quebec, Canada; Jean-Pierre Raynaud, Paris, France

[73] Assignee: Roussel Uclaf, France

[21] Appl. No.: 444,198

[22] Filed: May 18, 1995

Related U.S. Application Data

[62] Division of Ser. No. 347,054, Nov. 30, 1994, which is a division of Ser. No. 19,232, Feb. 18, 1993, Pat. No. 5,389,613, which is a division of Ser. No. 595,297, Oct. 10, 1990, Pat. No. 5,189,021, which is a division of Ser. No. 334,088, Apr. 5, 1989, Pat. No. 4,981,842, which is a division of Ser. No. 120,408, Nov. 13, 1987, Pat. No. 4,851,386, which is a division of Ser. No. 921,737, Oct. 22, 1986, Pat. No. 4,745,102, which is a division of Ser. No. 895,179, Aug. 11, 1986, Pat. No. 4,728,640, which is a division of Ser. No. 621,421, Jun. 18, 1984, Pat. No. 4,743,589, which is a division of Ser. No. 468,932, Feb. 23, 1982, Pat. No. 4,472,382, which is a division of Ser. No. 189,168, Sep. 22, 1980, abandoned.

[30] Foreign Application Priority Data

Sep. 21, 1979 [FR] France .................. 79 23545

[51] Int. Cl.$^6$ .................. A61K 38/00; C07K 14/00
[52] U.S. Cl. .................. 514/15; 514/800; 424/439; 424/445; 530/328
[58] Field of Search .................. 514/15, 800; 424/439, 424/445; 530/328

[56] References Cited

U.S. PATENT DOCUMENTS

| | | | |
|---|---|---|---|
| 3,835,108 | 9/1974 | Immer et al. | 260/112.5 |
| 3,880,825 | 4/1975 | Sakakibara et al. | 260/112.5 |
| 3,917,825 | 11/1975 | Matsuzawa et al. | 424/177 |
| 3,941,763 | 3/1976 | Sarantakis . | |
| 4,002,738 | 1/1977 | Johnson et al. | 260/112.5 |
| 4,005,194 | 1/1977 | Johnson | 260/112.5 |
| 4,010,261 | 3/1977 | Johnson et al. | 260/112.5 |
| 4,071,622 | 1/1978 | Johnson et al. | 260/112.5 |
| 4,234,571 | 11/1980 | Nestor et al. . | |
| 4,244,946 | 1/1981 | Rivier et al. | 424/177 |
| 4,472,382 | 9/1984 | Labrie et al. . | |
| 4,472,882 | 9/1984 | LaBrie et al. | 514/15 |
| 4,728,640 | 3/1988 | LaBrie et al. | 514/15 |
| 4,743,589 | 5/1988 | LaBrie et al. | 514/15 |
| 4,851,386 | 7/1989 | LaBrie et al. | 514/15 |
| 4,945,102 | 7/1990 | LaBrie et al. | 514/15 |
| 5,189,021 | 2/1993 | LaBrie et al. | 514/15 |
| 5,389,613 | 2/1995 | LaBrie et al. | 514/15 |

FOREIGN PATENT DOCUMENTS

| | | |
|---|---|---|
| 2465486 | 3/1981 | France . |
| 2836631 | 3/1979 | Germany . |
| 1547557 | 6/1979 | United Kingdom . |

OTHER PUBLICATIONS

B. Mitawi et al, The Effect of Immunization of Male Guinea Pigs M.J. Blend et al, Inter. Am. Conf. To Accup. Med. 1973, pp.190–198.

Chem. Abstr., vol. 94 (1981) p. 132895w 106348d, Mar. 1981 France.

Seguin et al, Chem. Abstracts, 94, 138(1981) Abst. No. 132,895w Labrie et al, Chem. Abstracts,96, 123 (1982) Abst. No. 1317c.

Antaki et al, L'Union Mederal du Canada 103, 1191–1201 (1974).

Jones et al, Chem. Abstracts,101, 86(1984) Abst. No. 33574.

Werlin et al, Chem. Abstracts, 99 109(1983) Abst. No. 16882u.

Sledman's Medical Dictionary, 23, Ed., The William & Wilkins Co.Balitmore, 1976.

Auclair et al, Biochemical and Biophysical Research Communications, vol.76, No.3, (1977) 855–862.

Fraser et al, Endocr. 63, (1974) 399–406.

Auclair et al, Endocr. 101, (1977) 1890–1893.

Geller et al, J. Endocr. 48, (1970) 289–290.

Schally et al, Am. J. Obstetries and Gynaecology, 114, (1972),423–442.

Rivier et al, Peptides, (1976), 427–451.

*Primary Examiner*—Cecilia J. Tsang
*Assistant Examiner*—P. Lynn Touzeau
*Attorney, Agent, or Firm*—Bierman, Muserlian and Lucas LLP

[57] ABSTRACT

A method of treating prostate cancer in warm-blooded animals comprising administering to warm-blooded animals an effective amount of a peptide of Formula I and an anti-androgen.

6 Claims, 16 Drawing Sheets

FIG. IG
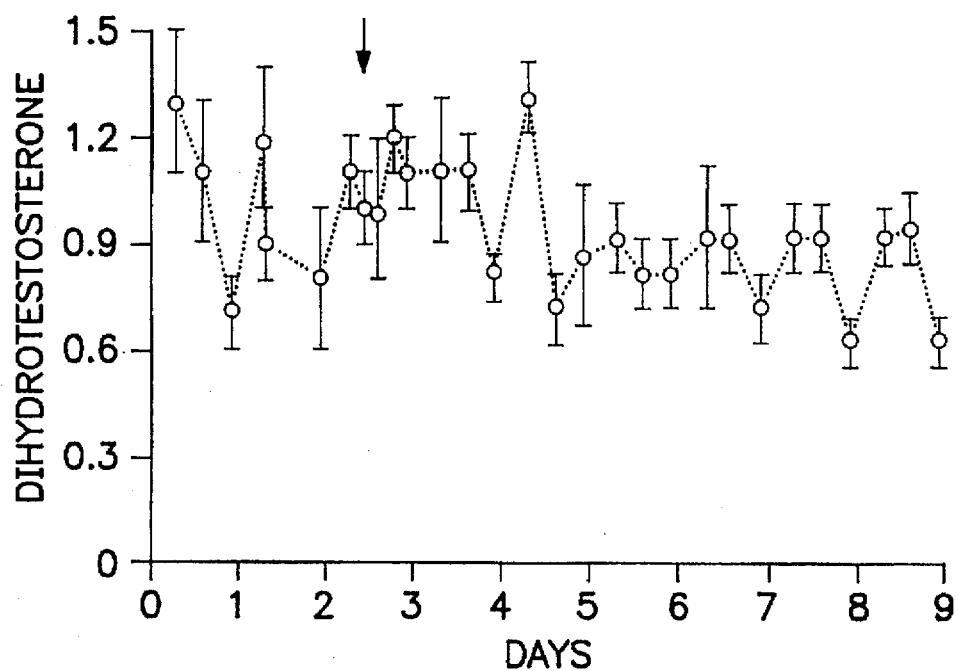
FIG. IH
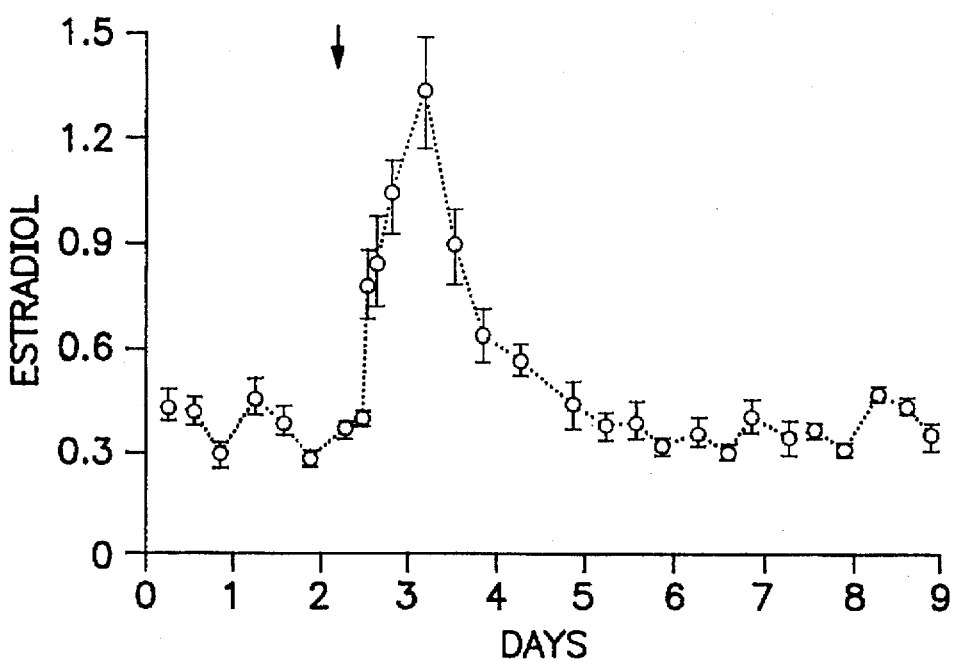

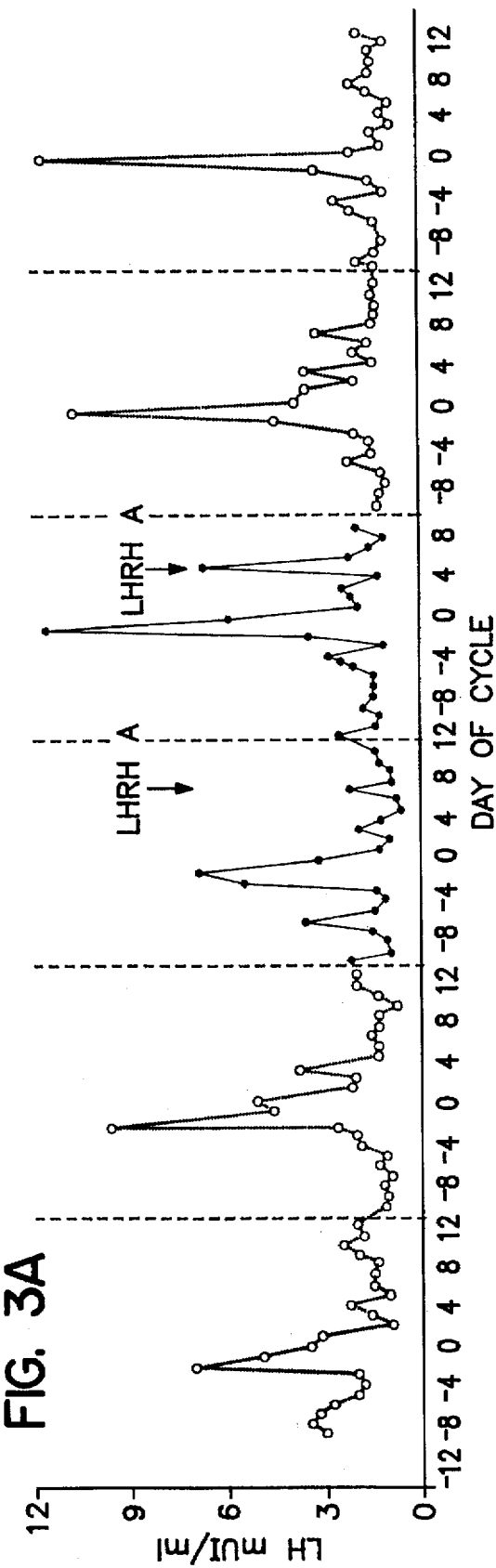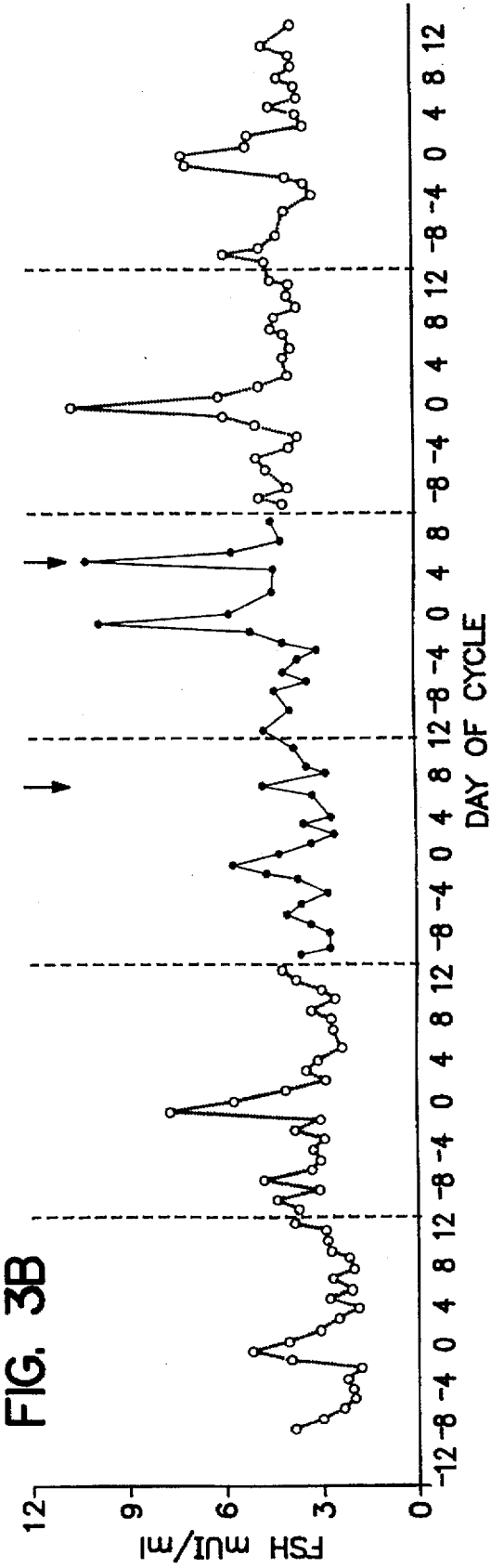

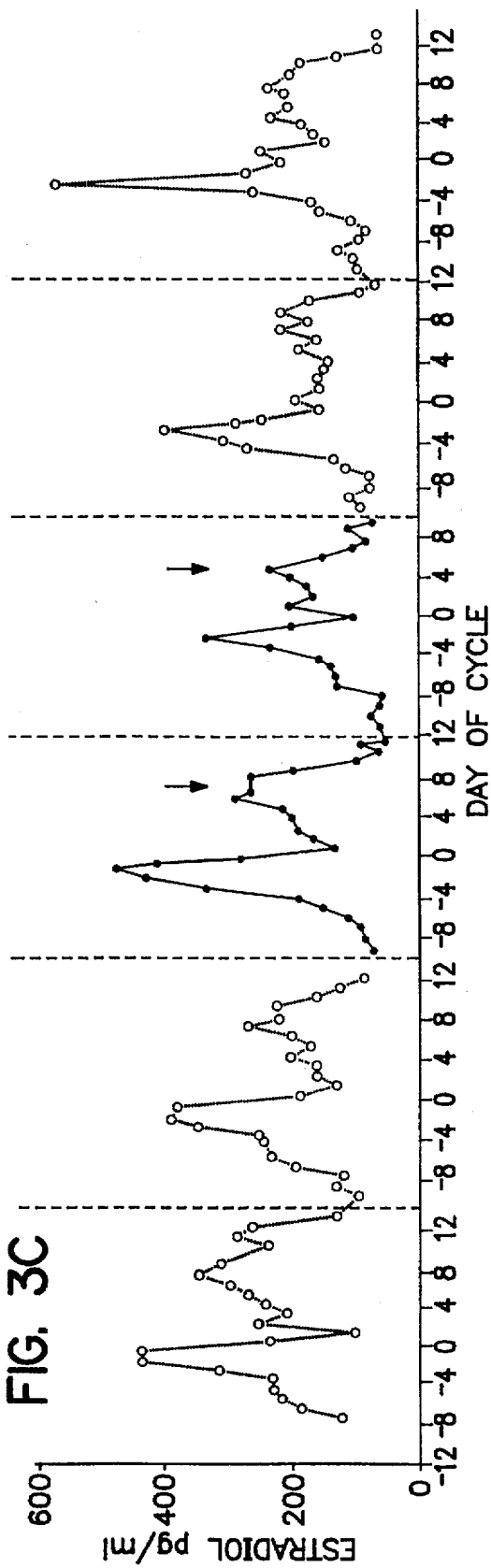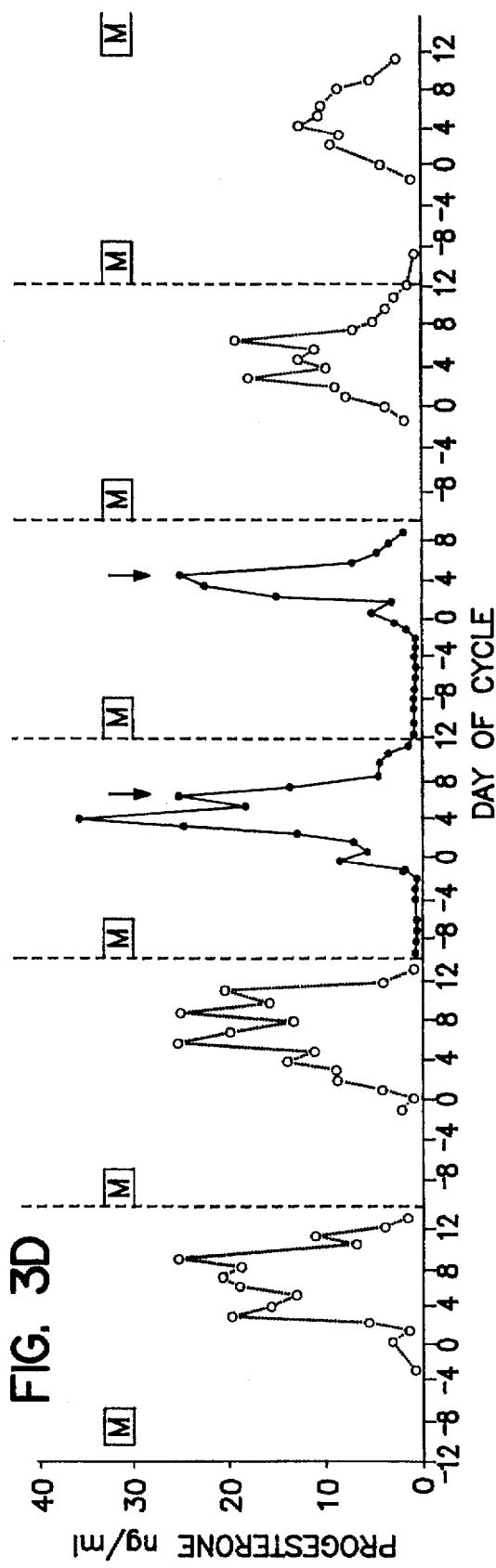

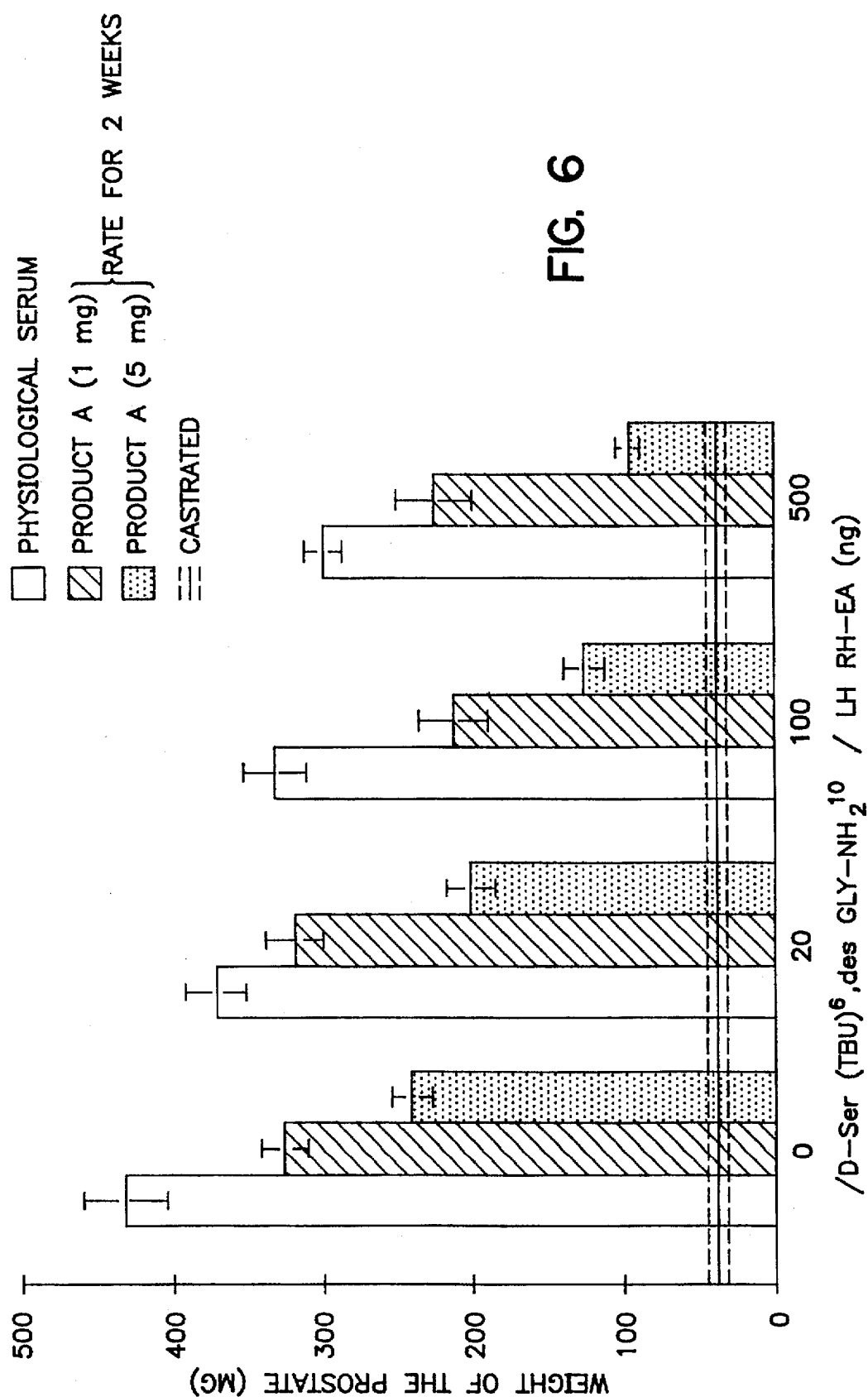

TREATMENT METHOD

PRIOR APPLICATIONS

This application is a division of U.S. patent application Ser. No. 347,054 filed Nov. 30, 1994, which is a division of U.S. patent application Ser. No. 019,232 filed Feb. 18, 1993, now U.S. Pat. No. 5,389,613 which is a division of U.S. patent application Ser. No. 595,297 filed Oct. 10, 1990, now U.S. Pat. No. 5,189,021 which is a division of U.S. patent application Ser. No. 334,088 filed Apr. 5, 1989, now U.S. Pat. No. 4,981,842 which is a division of U.S. patent application Ser. No. 120,408 filed Nov. 13, 1987, now U.S. Pat. No. 4,851,386 which is a division of U.S. patent application Ser. No. 921,737 filed Oct. 22, 1986, now U.S. Pat. No. 4,745,102 which is a division of U.S. patent application Ser. No. 895,179 filed Aug. 11, 1986, now U.S. Pat. No. 4,728,640 which is a division of U.S. patent application Ser. No. 621,421 filed Jun. 18, 1984, now U.S. Pat. No. 4,743,589 which is a division of U.S. patent application Ser. No. 468,932 filed Feb. 23, 1982, now U.S. Pat. No. 4,472,382 which is a division of U.S. patent application Ser. No. 189,168 filed Sep. 22, 1980, now abandoned.

STATE OF THE ART

The structure of LH-RH or the factor liberating lutelusiant hormone (LH) and the folliculostimulant-hormone (FSH) have been elucidated by Schally et al [BBRC, Vol. 43 (1971), p. 393 and 394]. LH-RH is a decapeptide of the formula (pyro) Glu-His-Trp-Scr-Tyr-Gly-Leu-Ary-Pro-Gly-$NH_2$ and secreted by the hypothalmus and is transported by adenohypophysis, where it stimulates liberation of LH and FSH. A number of agonists of LH-RH are described in the literature.

The compounds of formula I and their preparation are described in the literature in which the following is a partial list: Coy et al [LH-releasing activity of potent LH-RH analogs in vitro, BBRC, Vol. 67 (1975), p. 576–582], Vale et al in Hypothalmus and endocrine functions (Labric et al editors, Plenum Press) 1976), p. 397–429, Fujino [BBRC, Vol. 49 (1972), p. 863], German Patent NO. 2,509,783, Japanese Patent No. 49100-081, Belgium Patents No. 842, 857, No. 832,310 and No. 832,311 and U.S. Pat. Nos. 3,901,872, 3,896,104, 3,971,737 and 4,003,884. The nomenclature used for the peptides of formula I is that used in the said publications and patents.

OBJECTS OF THE INVENTION

It is an object of the invention to provide a novel method of treating prostate adenocarcinoma, prostate benign hypertrophia, endometriosis, dysmenorrhea, hirsuitism, homono-dependant mammary tumors, treatment and prevention of precocious puberty, induction of a retardation of the appearance of puberty and treatment of acne is warm-blooded animals, including humans, with a peptide of formula L.

These and other objects and advantages of the invention will become obvious from the following detailed description.

THE INVENTION

The novel method of the invention for the treatment of prostate adenocarcinoma, prostate benign hypertrophia, endometriosis, dysmenorrhea, hirsuitism, hormono-dependant mammary tumors, treatment and prevention of precocious puberty, induction of a retardation of the appearance of puberty and treatment of acne of mammals comprising administering to warm-blooded animals an effective amount of a peptide of the formula p-Gly-His-Trp-Ser-Tyr-X-Y-Arg-Pro-Z (I), where (a) Z is Gly-$NH_2$, Y is Leu and X is Gly, (b) Z is Gly-$NH_2$, Y is Leu, X is DN Leu, DN Val, D Abu (α-aminobutyric acid), D Phe, D Ser, D Thr, D Met, D Pgl, D Lys, Leu; Ile, Nle, Val, N Val, Met, Phe, D Leu, D Arg, D Ser (tbu), D Thr (tbu), D cys (tbu), D asp (Otbu), D Glu (Otbu), D Orn (boc), D Lys (boc), D Trp, Trp, 2-methyl Ala, D Tyr, D Met, ε-lauryl-D Lys, ε-dextran-D Lys (c) Z is NH-cyclopropyl or —NH-Alk wherein Alk is alkyl of 1 to 3 carbon atoms, Y is Leu and X is D Ser (tbu), D Thr (tbu), D Asp (Otbu), D Glu (Otbu), D Orn (boc), D lys (boc), (d) Z is —NH—$CH_3$, —NH—$CH_2$—$CH_3$, NH—$CH_2$—$CH_2$—$CH_3$, —NH—$CH_2$—$CH_2$—OH,

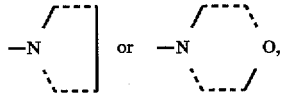

Y is Leu and X is Gly, (e) Z is —NH—$CH_2$—$CH_3$, Y is Leu and X is D Trp, D Leu, D Ala, D Ser (tbu), D Tyr, D Lys, Ala, (f) Z is Gly-$NH_2$ or —NH—$CH_2$—$CH_3$, Y is NaMe Leu and X is Gly, (g) Z is —NH-cyclopropyl, Y is Leu and X is D-Leu or (h) Z is Gly-$NH_2$, —NH-cyclopropyl or —NHAlk where Alk' is alkyl of 1 to 3 carbon atoms, Y is Ser (but), Cys (but), Asp (Obut), Glu (Obut), Orn (boc), Lys (boc) and X is Gly.

It has recently been discovered that modification of the level of production of testicular steroids and the relative production of testicular steroids among themselves is induced in humans by administration of D Ser (Tbu)[6] of Gly[10] LH-RH ethylamide as well as modification of the production level of ovarian steroids and the hormonal balance induced in females by administration of the same product.

The intranasal administration of a single dose of 500 μg of D Ser (Tbu)[6] or Gly[10] LH-RH ethylamide to a human provokes of lessening of the cyclicity of testicular steroids, especially of testosterone and a drop of seric levels of the steroids lasting for 3 days after administration of the product. A 50% diminution of the level of testosterone was noted on the 3rd day following the administration of the product and on the fourth day after the administration of the product, the level returned to normal as can be seen from the clinical data furnished herein.

A desensitizing effect of this type of product would be secondary to the liberation of endogenous LH. It is also possible that the peptides act directly on the testicular level.

Without being limited to the discussions of the action of the product of formula I used in the method of the invention, it is believed that the effects obtained in the treatment of adenocarcinoma and prostate hypertrophia, for example, is due to the modification of the level of production of testicular steroids and the relation of the ratio of the steroids among themselves.

More precisely, it is thought that the method of biosynthesis and degradation of testicular androgens is modified by administration of the compounds of formula I. It is well understood that other phenomena can intervene in this complex protease and the method of the invention is not intended to be limited by the above discussion.

In a preferred embodiment of the invention, an effective amount of a peptide of formula I is administered for the treatment of adenocarcinoma or benign hypertrophia of the prostate in male mammals having androgeno-dependent effections.

Until now, one tried to diminish androgenic activity of testosterone in patients with cancer of the prostate by administration of antiandrogens, estrogens and progestatives. The classical treatment of cancer of the prostate consists of administration of estrogens which blocks the liberation of LH but the organism may become adapted to treatment by an escape phenomena. To maintain the effect of the treatment, it is necessary to increase the dosage but the administration of strong doses of estrogens provokes a vascular thrombosis risk or other vascular complications. The classical treatment used until now cannot be used without major difficulties.

Another therapeutic approach consists of administering antiandrogens and for the first time, the antiandrogens block the androgenic steroidal receptors and lessen the effection of androgeno-dependence. However, this produces a competition of the antiandrogens with testosterone on the hypophysial level which induces a level of inhibition caused by testosterone with the liberation of LH and FSH. As a result of this, there is provoked an increase of LH and FSH and therefore of testosterone. The antiandrogen administration is not sufficient therefore to block perpherial androgen receptions. As a result thereof, the progressive increase in the production of testoserone neutralizes the initial effect of the antiandrogens. The treatment of cancer of the prostate by administration of antiandrogens has not proved to be sufficient.

It has also been tried to control the level of testosterone by administration of progestatives which also block the release of LH but these products have only a little activity in humans. Progestatives provoke primarily an effect on their androgen component which limits again the interest in their utilization.

When the failure of hormonal treatments were known, one resorted to the classical chemio-therapy of cancer (antimitotics, for example) or radiotherapy or castration. Therefore, the search for an effective hormonotherapy has continued especially for the elimination to a maximum the seretion of androgens by a method other than castration.

In a modification of the method of the invention, the compounds of formula I are administered in association with a steroidal or non-steroidal antiandrogen, especially with 5,5-dimethyl-3-[4-nitro-3-trifluoromethyl-phenyl]-2,4-imidazolidinedione or with 2-methyl-N-[4-nitro-3-trifluorophenyl]-propanamide. The two latter products are administered to humans at a dose, for example, of 10 mg to 1 g per day orally or by injection in association with product of formula I.

In this latter method, the advantage of the association of an antiandrogen and an agonist of LH-RH are as follows: a lower dose of the antiandrogen is required to neutralize the androgens of testicular origin; the antiandrogen neutralizes also androgens of surrenalenal origin; and the treatment with the agonist of LH-RH by inhibition of the secretion of gonadotrophinal prevents the phenomenon of escape caused by the use of an antiandrogen alone.

Another preferred embodiment of the invention comprises the administration of an effective amount of a compound of formula I for the treatment or prevention of precocious puberty or the induction of a retardation of puberty in male mammals as well as for treatment of acne in male mammals. A preferred embodiments of the said method involves the administration of the peptide of formula I in association with an steroidal or non-steroidal antiandrogen, such as the compounds mentioned above.

Another preferred method of the invention is for the treatment of endometriosis, of dysmenorrhea, of hirsuitism, for the treatment or prevention of precocious puberty or the induction of a retardation of puberty or for the treatment of acne in female mammals by the administration of an effective amount of a peptide of formula I.

The method of treatment of the invention is equally useful for the treatment of endometriosis, of dysmenorrhea, affections in which there is implicated an alteration of the estrogen/progesterone hormonal balance, in the treatment of hirsuitism, affection due to a hypersecretion of androgens and in the treatment or prevention of precocious puberty or in the induction of a retardation of the appearance of puberty in female mammals.

In a preferred mode of treatment of the invention, there is administered an effective amount of a peptide of formula I wherein Z is —NH—$CH_2$—$CH_3$, Y is Leu and X is D Trp, D Leu, D Ala, D Ser (Tbu), D Tyr, D Lys, Ala and preferably the peptide is D Ser (Tbu)$^6$ of Gly LH-RH ethylamide. This latter embodiment is especially useful for the treatment of hormonal-dependent mammalarian tumors in female mammals.

In the method of the invention, the peptides of formula I may be administered orally, parenterally or intranasally and depending on the product administered and the method of administration, the usual daily dose is 10 to 100,000 µg for male and female humans. In animals, the administered dose is a corresponding weight dose.

The efficacity of the products of formula I is proportional to the activity of liberation of genadotrophins by the said compounds. When the product is administered intranasally, it is estimated that the dose to be administered is 10 to 20 times greater than the dose required if the product were administered parenterally.

In a preferred method of the invention for the method of treatments referred to above, the daily dose of the compound of formula I is 10 to 10,000 µg when administered parenterally or 100 to 100,000 µg when administered intranasally to men and women. In the preferred embodiment of the invention administering D Ser (Tbu)$^6$ of Gly$^{10}$ LH-RH ethylamide, the daily dose is 10 to 200 µg parenterally or 100 to 2,000 µg intranasally.

The compounds of formula I are to be administered daily and the method of treatment of the invention includes the administration of compounds of formula I once or twice each day every day. The product of formula I may also be administered as spaced, sequential doses and the method of treatment of the invention includes administering a compound of formula I once or twice a day for a plurality of days at intervals. The compounds of formula I may be administered, for example, at spaced intervals of a few hours, of 2, 4, 8 or 15 days or a month. The compounds of formula I, for example, may be administered twice daily (at the two principle meals, for example), daily, twice-weekly, weekly, bi-monthly or monthly.

BRIEF DESCRIPTION OF THE DRAWINGS

FIGS. 1A to 1H are graphs of plasmatic levels of the results of Example 1.

FIGS. 3A to 3D, 4 and 5A are graphs of the levels of the results of Example 3.

FIGS. 6 and 7 are graphs of the prostate and seminal vesicles of treated rats from the results of Example 4.

Figure 1A:
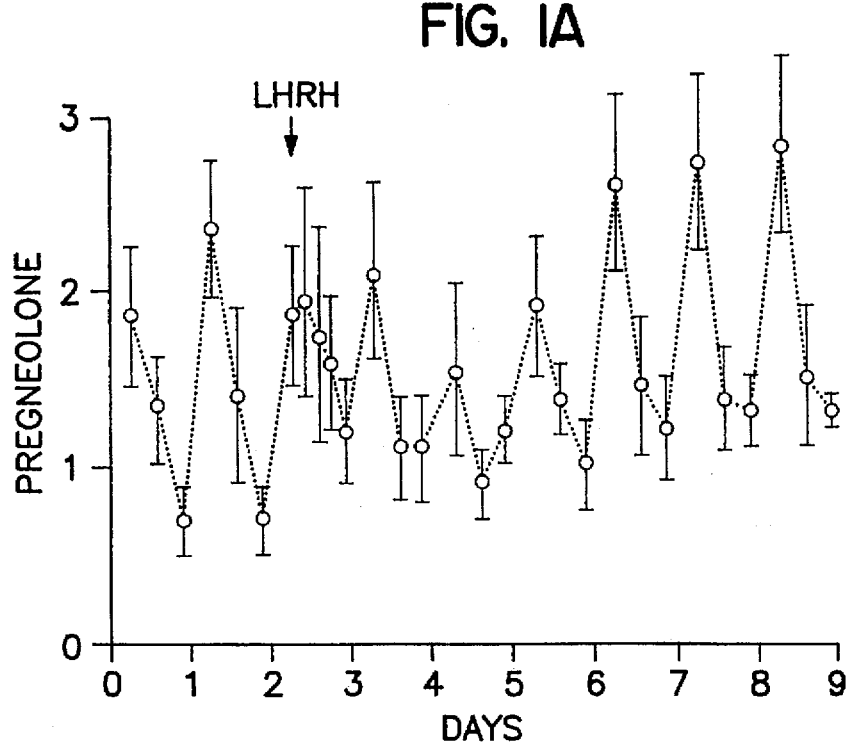
Figure 1B:
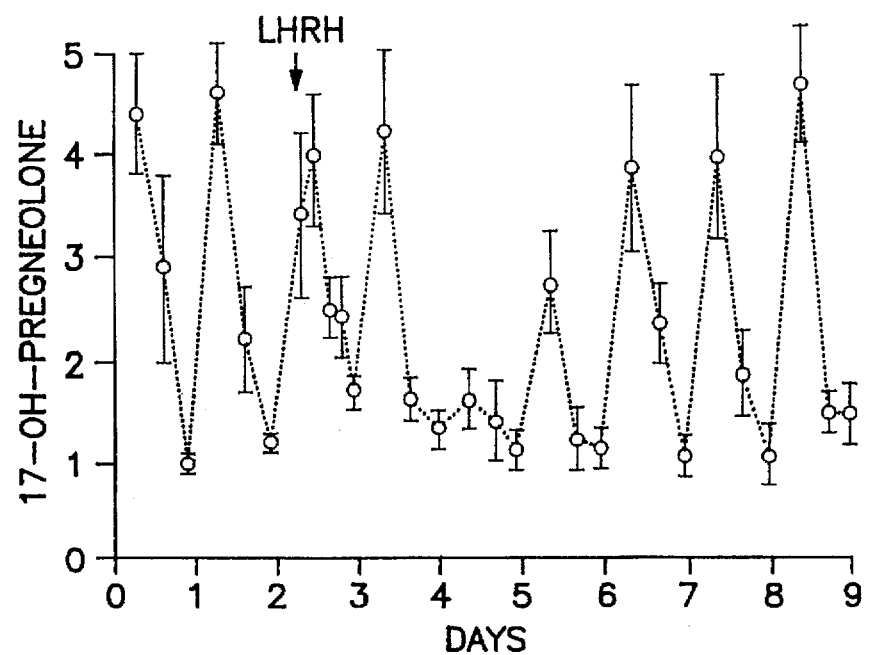
Figure 1C:
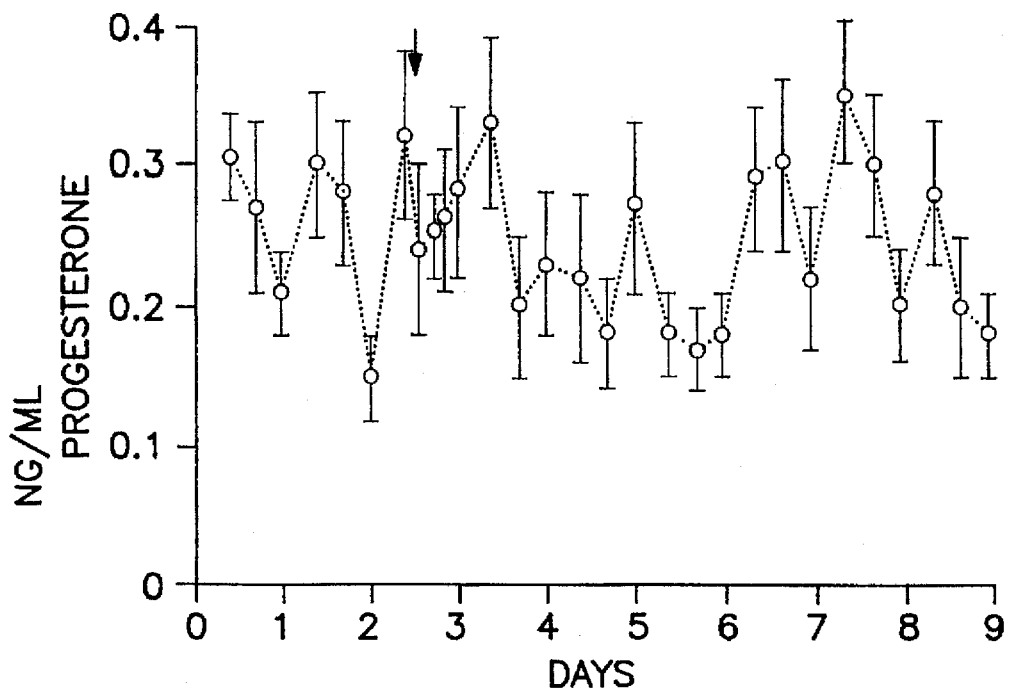
Figure 1D:
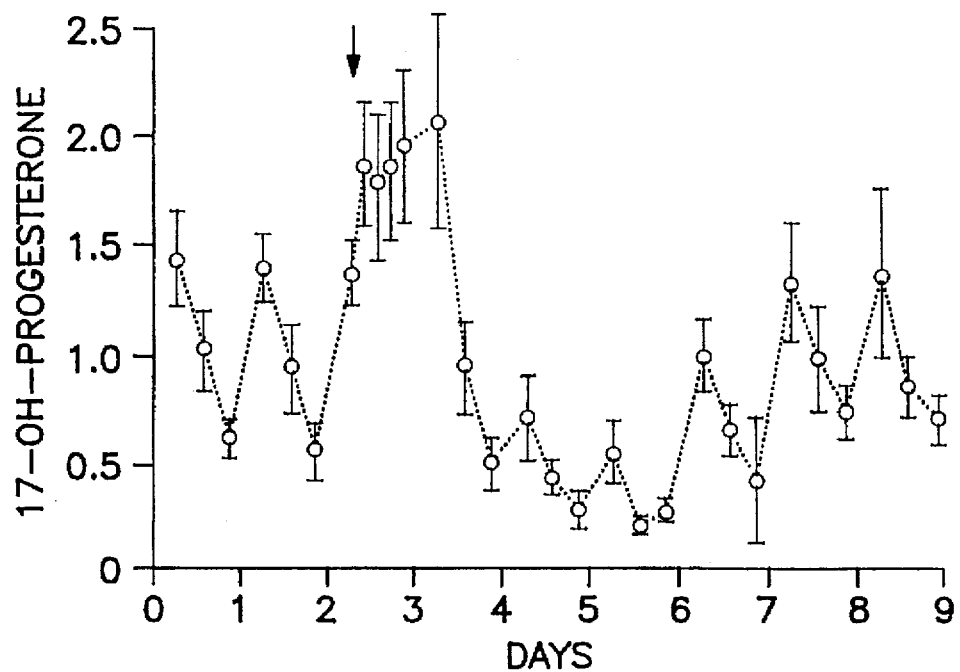
Figure 1E:
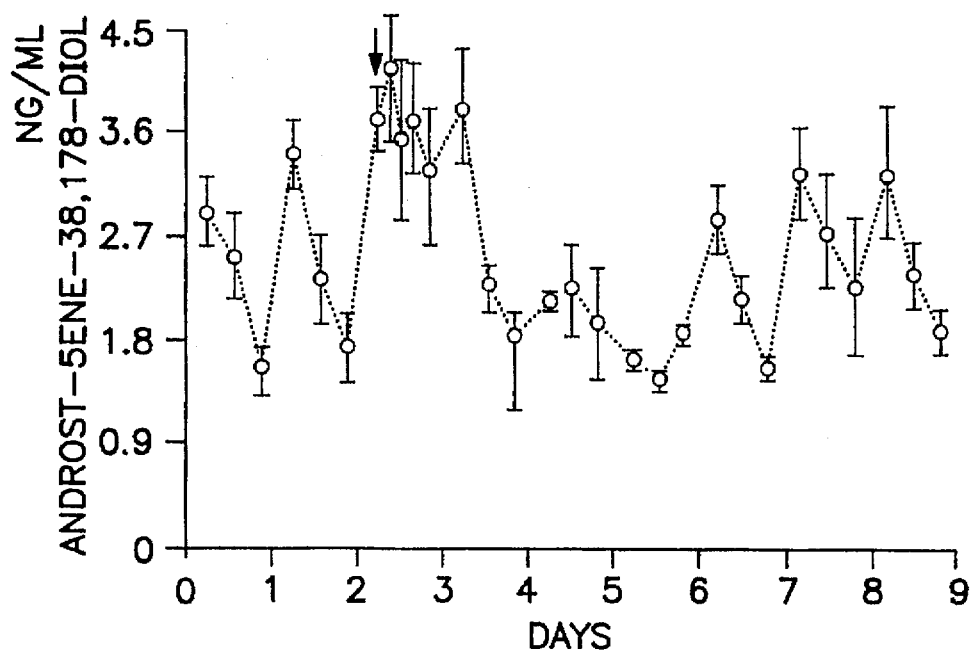
Figure 1F:
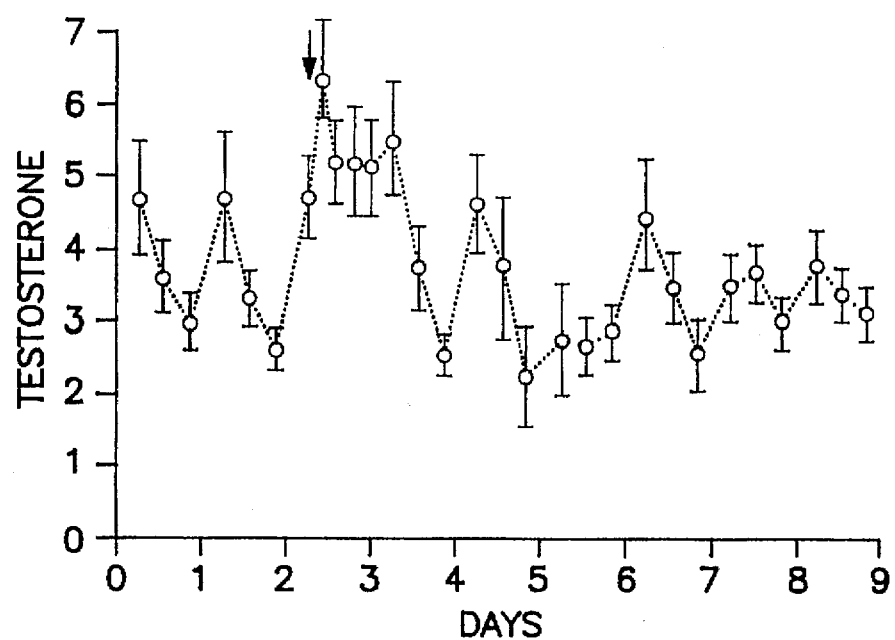
Figure 2A:
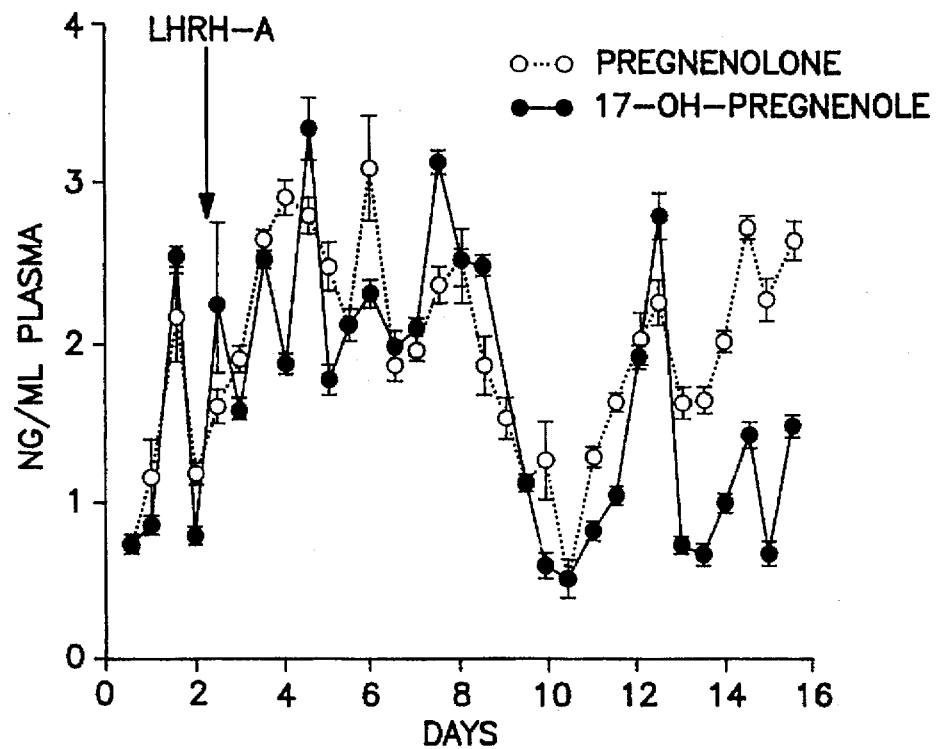
FIGS. 2A to 2D are graphs showing the diminution of androgenic steroids and the level of testosterone of the results of Example 2.
Figure 2B:
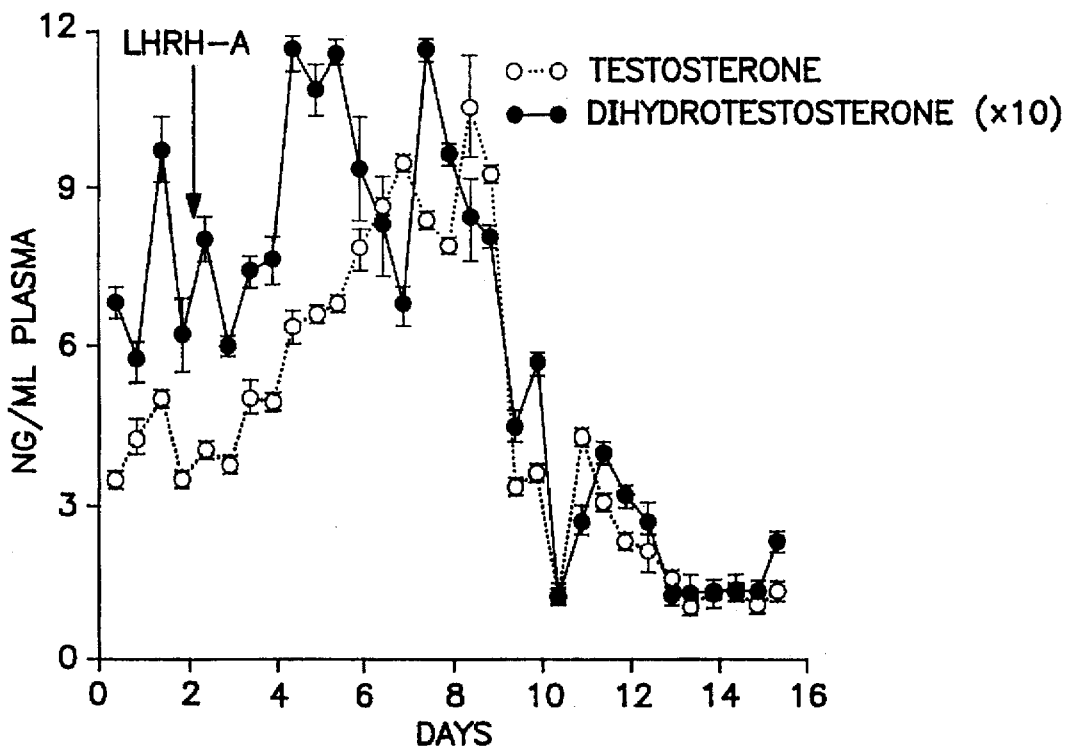
Figure 2C:
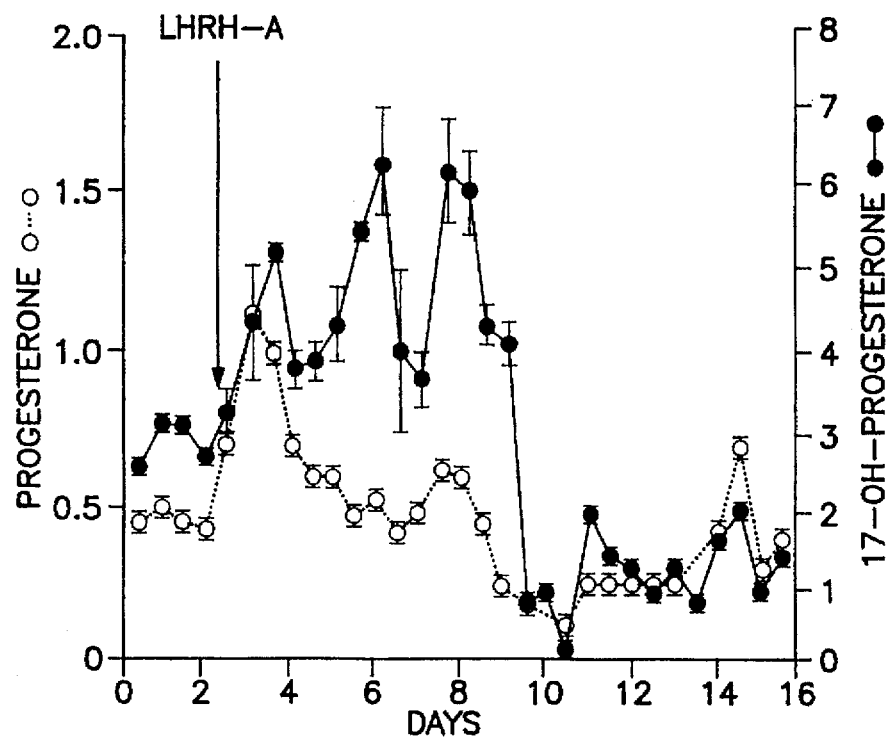
Figure 2D:
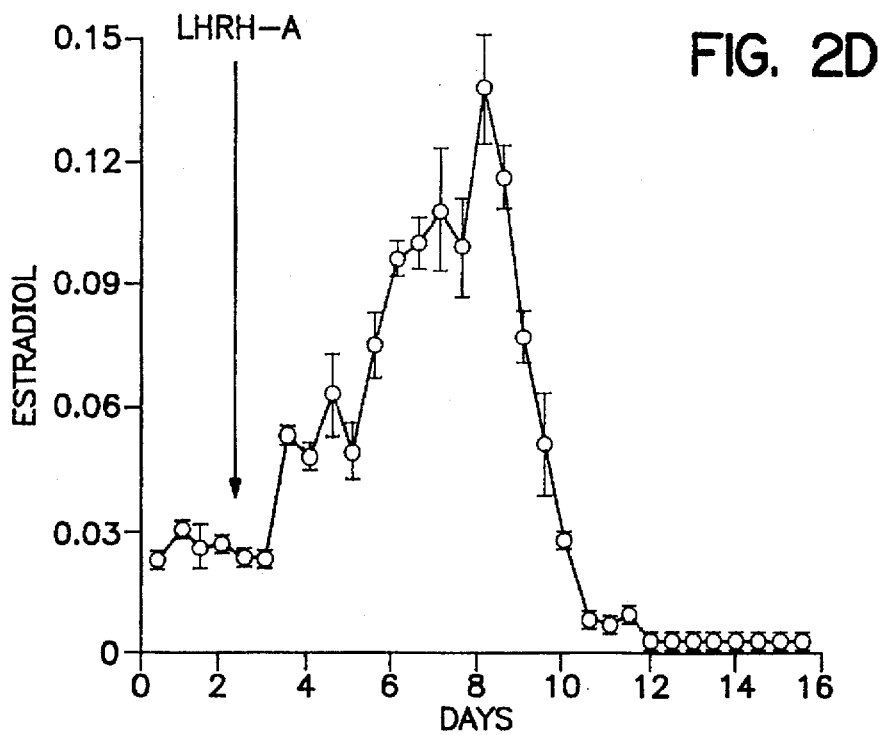
Figure 4A:
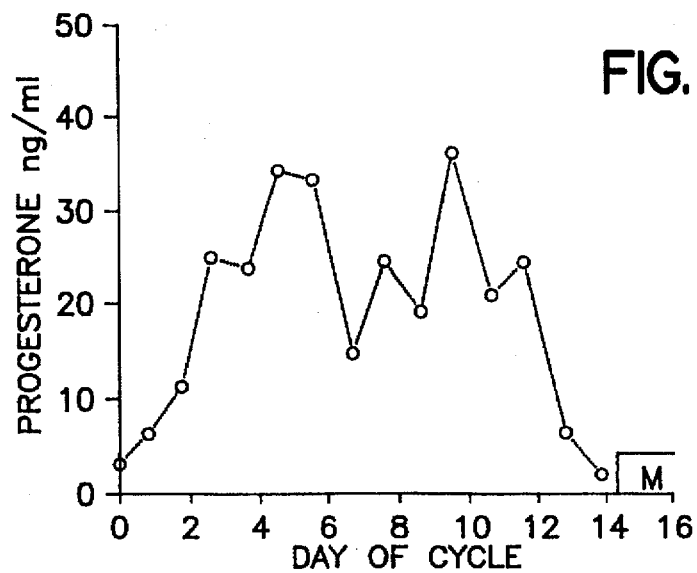
Figure 4B:
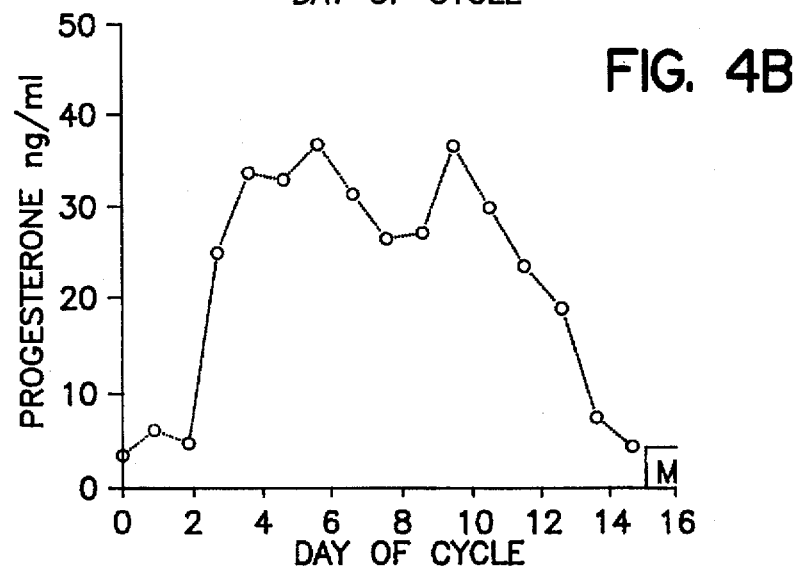
Figure 4C:
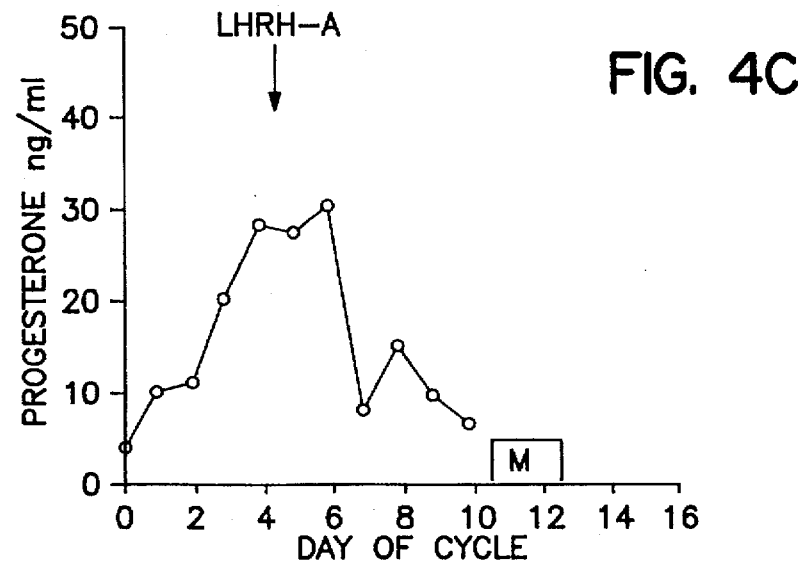
Figure 4D:
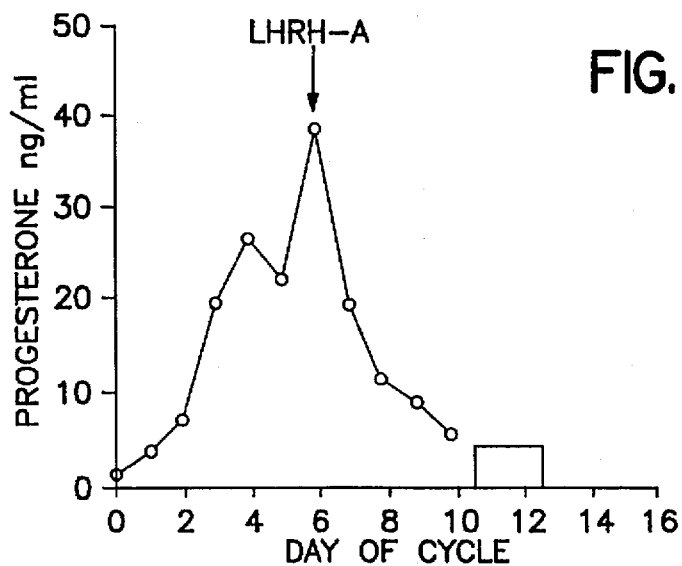
Figure 4E:
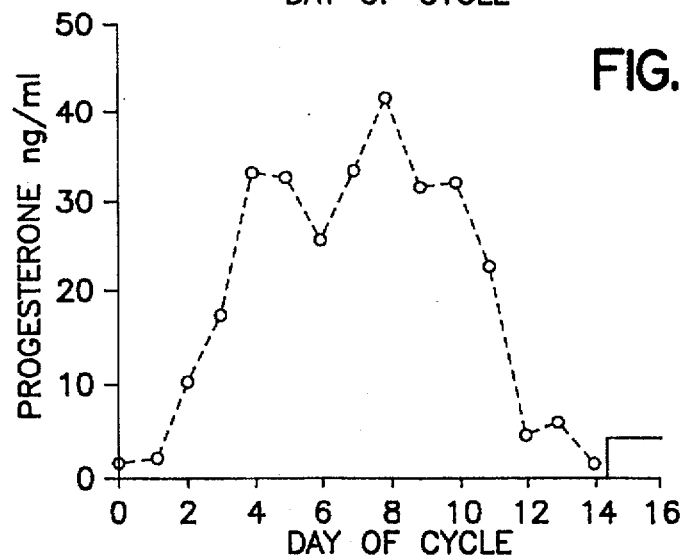
Figure 4F:
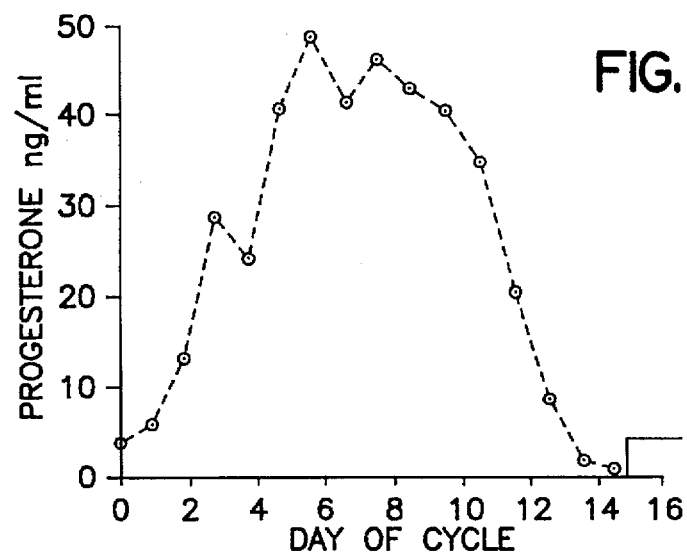
Figure 5A:
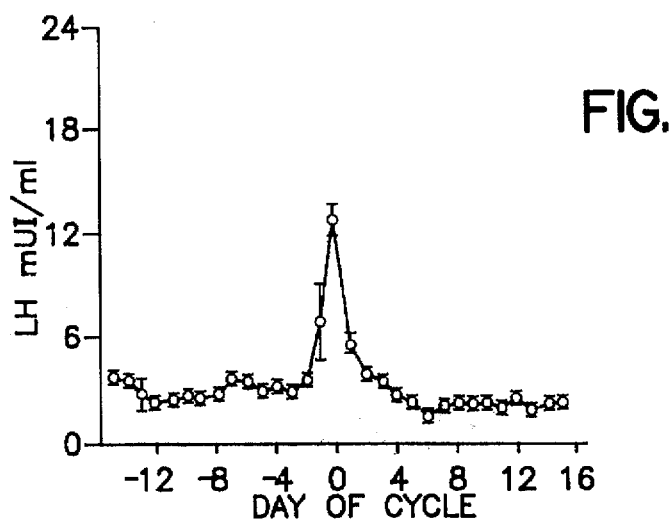
Figure 5B:
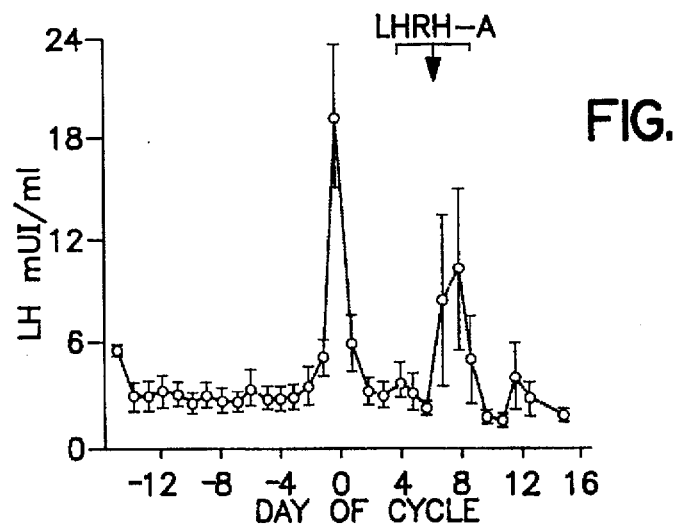
Figure 5C:
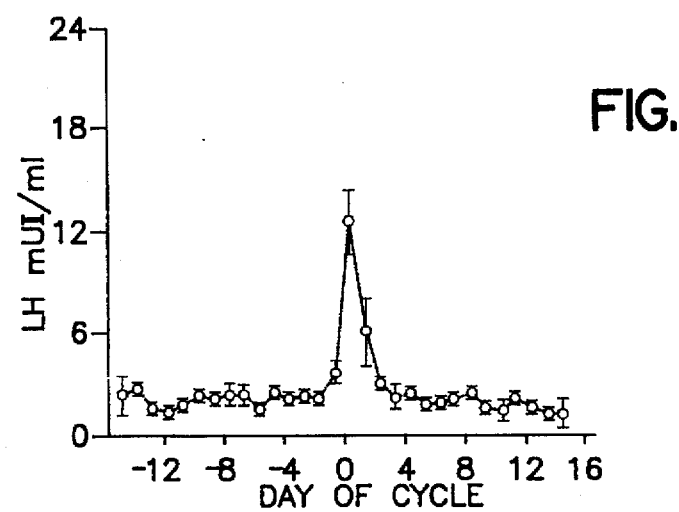
Figure 5D:
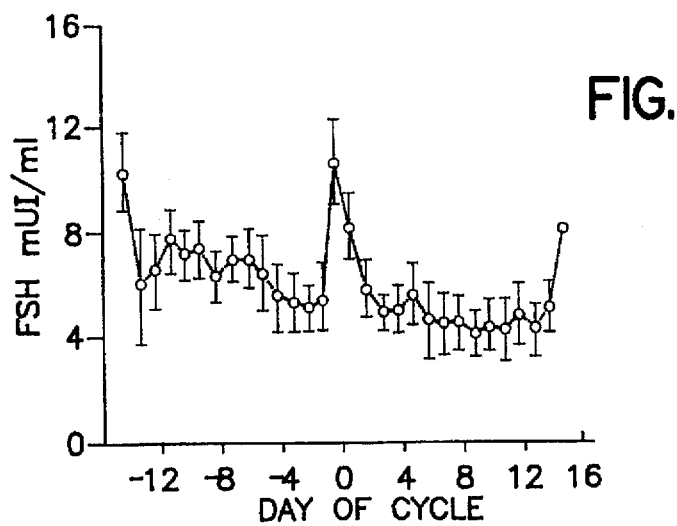
Figure 5E:
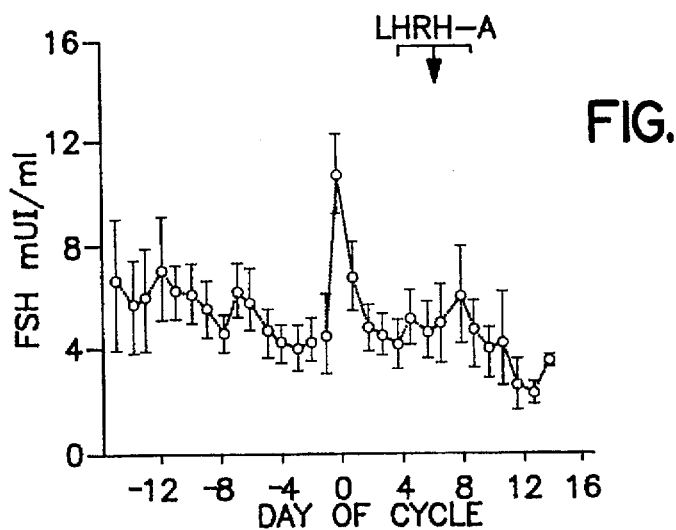
Figure 5F:
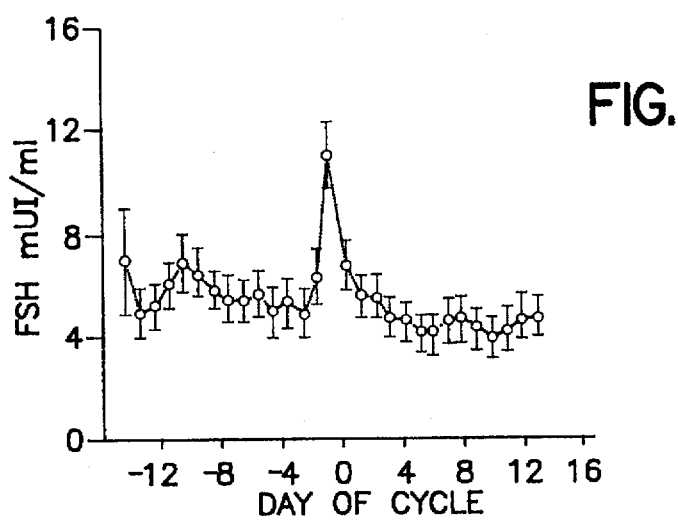
Figure 5G:
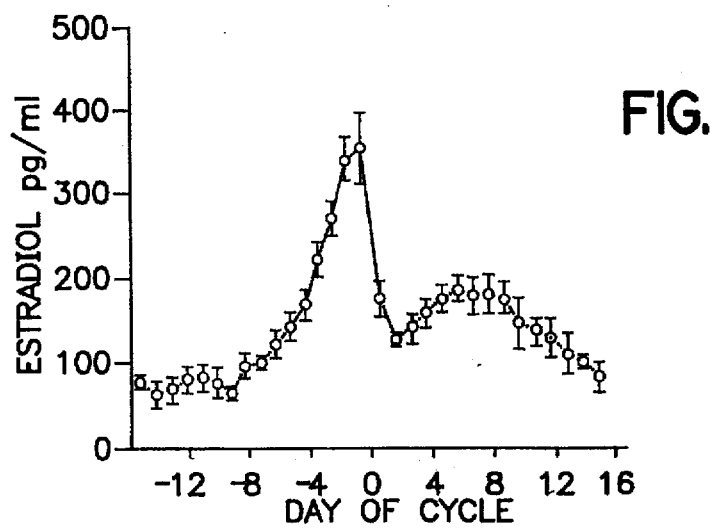
Figure 5H:
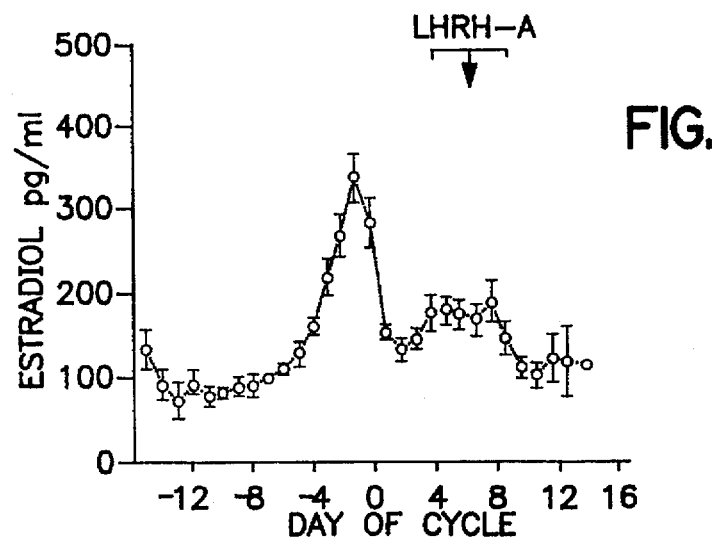
Figure 5I:
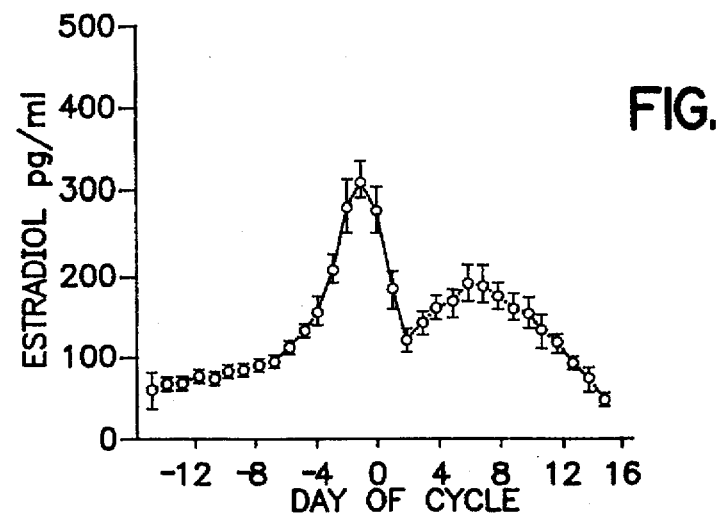
Figure 5J:
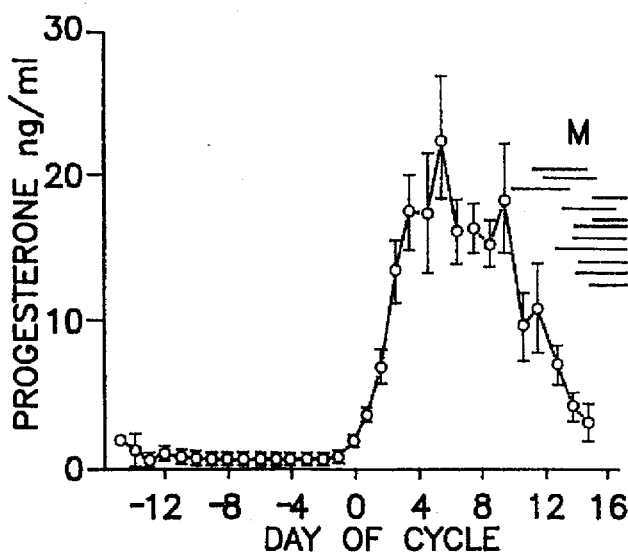
Figure 5K:
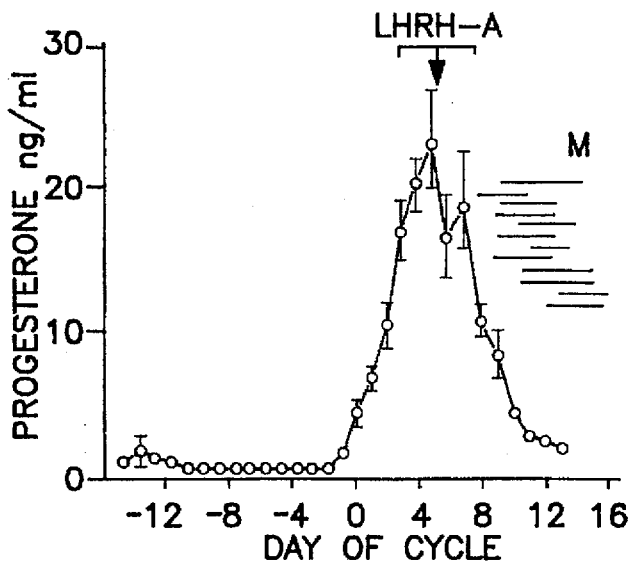
Figure 5L:
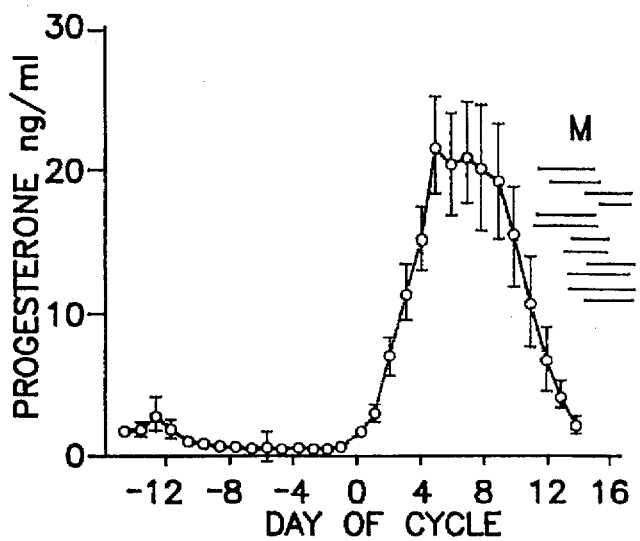
Figure 7:
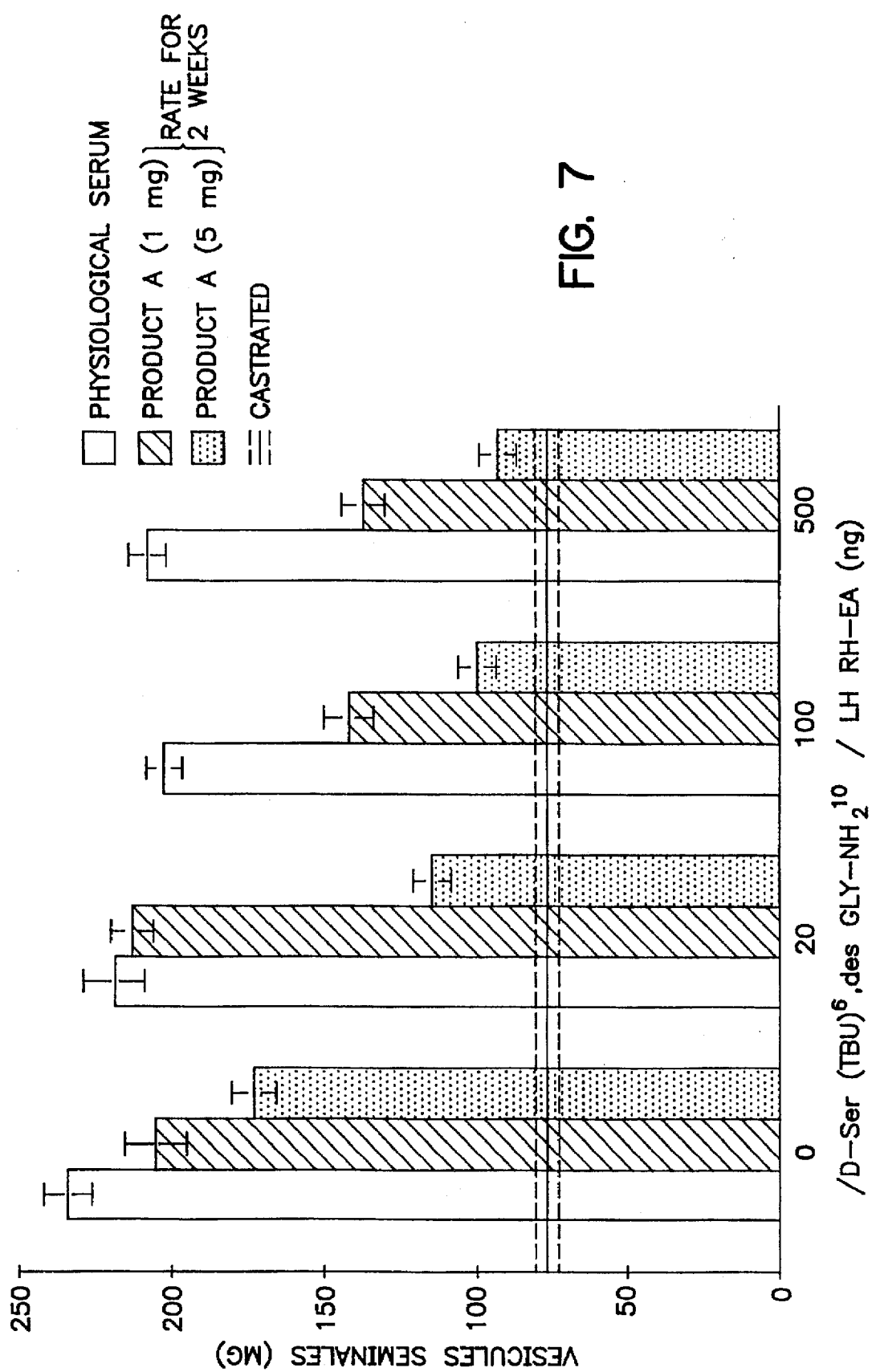

In the following examples there are described several preferred embodiments to illustrate the invention. However, it is to be understood that the invention is not intended to be limited to the specific embodiments.

EXAMPLE 1

The inhibitory activity of D Ser (Tbu)$^6$ or Gly$^{10}$ LH-RH ethylamide (described in German application Ser. No. 2,438, 350) against testicular steroidogensis in men in good health was determined on men in good health aged 30 to 40 years. The said product was administered intranasally at a dose of 500 µg in a few drops of distilled water at 8 A.M. on the third day of the test. For 2 days prior to the treatment and for 6 days after the treatment, samples of blood were taken daily at 8 A.M., 3 P.M. and 10 P.M. On the day of administration of the LH-RH agonist, blood samples were taken at 11 A.M. and 6 P.M.

The seric concentrations of LH and FSH were measured by radioimmuno-logic dosages with double antibodies and the antibodies for measuring LH and FSH were furnished by the National Pituitary Agency of N.I.H. in Bethesda, Md. The seric concentrations of steroids was measured by radioimmuno-logic dosages in which one ml of serum was extracted with ether and the steroids were separated on a LH-20 column before measuring with radioimmuno-logic dosages. The radioimmuno-logic dosage results were determined by a program derived from model II of Rodbard et al [Second Karolinska Symposium on Research Methods in Reproductive Endocrinology, Diezfalusky Editer, Copenhague (1970), p. 79–103]. The statistical significance was determined by the "multiple level test" of Duncan-Kramer [Kramer, Biometrics, Vol 12 (1956), p. 307]. The results are shown in the graphs on sheet 1 of the Figures filed herewith.

From the said graphs, it can be ascertained that the intranasal administration of 500 µg of D Ser (Tbu)$^6$ of Gly$^{10}$ LH-RH ethylamide provoked an increase of LH and FSH in plasmatic levels with a return to normal levels 8 to 12 hours after the administration of the peptide. The level of all steroids measured at an elevated level at 8 hours and at a lower level at 22 hours than the level obtained two days before the treatment.

The said intranasal administration led to a modification of the daily cycle of the level of steroids. On the day of treatment, the seric concentration of pregnenolone, 17-OH-pregnenolone, progesterone, 17-OH-progesterone, $\Delta^5$-androstene-3β,17β-diol and testosterone increased and then this elevation was followed by a diminution of the cycle and a drop of seric level of the steroids for the following 3 days. The concentration of testosterone and 17-OH-progesterone had fallen to 50 and 40%, respectively, to the initial control values on the 3rd day following the peptide administration. A return to normal levels was observed on the fourth day and until the 6th day following the treatment. There is observed a very different profile for the curve of the seric concentration of 17β-estradiol with a progressive increase starting about midway after the administration of the peptide, then a deffered elevation of 20 to 35 to 100 to 250 µg/ml in different subjects on the day after treatment while the return to normal is interposed more slowly. Therefore, the administration of a strong agonist of LH-RH to man leads to an inhibition of testicular steroidogenesis.

The lessening of the periodicity and the drop of seric levels of testosterone and its precursors lasts for a duration of 3 days following a single intranasal administration of D Ser (Tbu)$^6$ of Gly$^{10}$ LH-RH ethylamide. The phenomena of daily variation of seric testosterone in humans is well known, for example, Dray et al [Rhyme biologique de la testosterone libre du plasma chez l'homme adulta sain; existence d'une variation circadienne, C-R Acad. Sci. Paris, Vol. 261 (1965), p. 573].

It can be seen from the above results that the rythmicity may be extended to pregnenolone, progesterone, 17-hydroxy-progesterone and $\Delta^5$-androstene-3β,17β-diol. The results also indicated the necessity of taking blood samples many times per day for an accurate estimation of the secretion of steroids as was done in the case of this study.

EXAMPLE 2

The inhibitory activity of D Ser (Tbu)$^6$ of Gly$^{10}$ LH-RH ethylamide on testicular steriodogenosis was determined on a patient with prostate cancer and the said product was intranasally administered twice a day at a dose of 500 µg and the evolution of level of plasmatic steroids was observed with the samples and levels being determined as in Example 1. The results are reported in the graphs of sheet 2 of the Figures. The said graphs show a diminution of the androgenic steroids and the level of testosterone, for example, was stabilized at a very low level in the two weeks of treatment.

EXAMPLE 3

The inhibitory activity of D Ser (Tbu)$^6$ of Gly$^{10}$ LH-RH ethylamide on ovarian steroidogenosis in women was determined on 6 women aged 36 to 35 years with normal and regular menstrual cycles and without prior endocrinal or gynecological problems. The study was conducted for 6 consecutive cycles consisting of 2 pretreatment cycles, 2 treatment cycles and 2 post-treatment cycles. Two drops of a solution containing 500 µg of D Ser (Tbu)$^6$ of Gly$^{10}$ LH-RH ethylamide were deposited on each nostril at 8 A.M. and 5 P.M. of a day between the 4th and 9th day after the peak of LH-day 0. Daily blood samples were taken between 4 and 6 P.M. to measure seric levels of LH, FSH, progesterone and estradiol which were determined by radioimmuno-logic tests with double antibodies. The antibodies to measure LH and FSH were furnished by the National Pituitary Agency of N.I.H. of Bethesda, Md.

Estradiol and progesterone were measured with highly specific antibodies developed against 7-(O-carboxymethyl)-oxime of estradiol and 12-(O-carboxymethyl)-oxime of progesterone, respectively [3H] 17β-estradiol and $^{125}$I-progesterone-12-[O-carboxymethyl)-oxime] used as tracers. The serum was extracted with benzene and the steroids were separated with a LH-20 column before the determination. The radioimmunological results were exploited by the program derived from model II of Rodbard and Lewald as in Example 1 and the statistical significance was measured by the multiple level test of Ducan-Kramer of Example 1. The results are shown in the graphs of sheets 3 to 5 of the Figures.

The graphs of sheet 3 illustrate typical levels of LH, FSH, 17β-estradiol and progesterone for 6 consecutive cycles and in the course of the 2 cycles of treatment, the seric levels of progesterone were reduced by 13 and 34%, respectively, as compared to the controls. Typical changes in the seric progesterone levels are more easily seen from the graphs of sheet 4. An accelerated diminution of the level of seric progesterone is observed for the 2 cycles of treatment with a return to normal for the 2 cycles of post-treatment.

Although there is for a few women of sheet 3 a diminution of the level of seric progesterone in the 2 cycles of post-treatment, the level of progesterone is normal if compared with 12 cycles of pretreatment and 12 cycles of post-treatment. Using the cycles of pretreatment as a base of 100%, the cycles of treatment and post-treatment are 46 and 99%, respectively, of the control values.

The review of all the results in the graphs of sheet 5 show the hormonal profile of 12 cycles of pretreatment, treatment and post-treatment. The level of progesterone after administration of D Ser (Tbu)$^6$ Gly$^{10}$ LH-RH ethylamide was reduced by 46% as compared to the controls (scale 13 to 127%).

EXAMPLE 4

The effect of the administration of D Ser (Tbu)$^6$ of Gly$^{10}$ LH-RH ethylamide in association with an antiandrogen was determined on groups of 9 normal rats of the Sprague-Dawley strain weighing about 250 g. The rats received for 14 days a subcutaneous administration at 9 A.M. of D Ser (Tbu)$^6$ of Gly$^{10}$ LH-RH ethylamide at a dose of 20, 100 or 500 µg in physiological serum and at 9 A.M. and 4 P.M. doses of 1 or 5 mg of 5,5-dimethyl-3-[4-nitro-3-trifluoromethyl-phenyl]-2,4-imidazolidinedione (product A) in solution in sesame oil containing 5% of benzyl alcohol. One group of rats received only physiological serum and one group received only product A.

The animals were killed 24 hours after the last injection and the weight of the prostate and seminal vesicles of the rats were determined. The results are shown in the graphs of sheets 6 and 7 of the Figures.

The results show that the weight of the seminal vesicles of rats treated with 100 or 500 µg of the peptide and 5 mg of product A approached the weight of the seminal vesicles of castrated rats. Similar, but a little less marked, results can be seen from the weight of the prostate.

Various modifications of the method of the invention may be made without departing from the spirit or scope thereof and it is to be understood that the invention is intended to be limited only as defined in the appended claims.

We claim:

1. A method for treatment of prostate adenocarcinoma and prostate benign hypertrophia in male warm-blooded animals comprising administering to such male animals an effective amount of an association of an antiandrogen and an agonist of LH-RH.

2. The method of claim 1 wherein the antiandrogen is non-steroidal.

3. The method of claim 1 wherein the antiandrogen is steroidal.

4. A method for treatment of prostate adenocarcinoma and prostate benign hypertrophia in male warm-blooded animals comprising administering to such male animals an effective amount of an antiandrogen and an agonist of LH-RH.

5. The method of claim 4 wherein the antiandrogen is non-steroidal.

6. The method of claim 4 wherein the antiandrogen is steroidal.

* * * * *

UNITED STATES PATENT AND TRADEMARK OFFICE
CERTIFICATE OF CORRECTION

PATENT NO. : 5,712,251
DATED : January 27, 1998
INVENTOR(S) : LABRIE et al

It is certified that error appears in the above-identified patent and that said Letters Patent is hereby corrected as shown below:

On the title page: Item

[ * ] Notice - The term of this patent shall not extend beyond the expiration date of Patent No. 4,472,382.

Signed and Sealed this

Fifth Day of January, 1999

Attest:

Attesting Officer

Acting Commissioner of Patents and Trademarks

UNITED STATES PATENT AND TRADEMARK OFFICE
CERTIFICATE OF CORRECTION

PATENT NO. : 5,712,251
DATED : January 27, 1998
INVENTOR(S) : LABRIE et al

It is certified that error appears in the above-indentified patent and that said Letters Patent is hereby corrected as shown below:

On the title page item,

[73] to read as --Assignee: Roussel Uclaf, France and Schering Plough Corporation, United States.--

Signed and Sealed this

Ninth Day of November, 1999

Attest:

Q. TODD DICKINSON

Attesting Officer

Acting Commissioner of Patents and Trademarks